US007237504B2

(12) United States Patent
Davis et al.

(10) Patent No.: US 7,237,504 B2
(45) Date of Patent: *Jul. 3, 2007

(54) DETECTION OF ODORS USING INSECTS

(75) Inventors: Paul James Davis, Bedford (GB); Lester Wadhams, Hertfordshire (GB); Justin Sheldon Bayliss, Worcester (GB)

(73) Assignee: Inscentinel Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/497,571

(22) PCT Filed: Dec. 20, 2002

(86) PCT No.: PCT/GB02/05879
§ 371 (c)(1),
(2), (4) Date: Jun. 3, 2004

(87) PCT Pub. No.: WO03/056292
PCT Pub. Date: Jul. 10, 2003

(65) Prior Publication Data
US 2005/0009444 A1    Jan. 13, 2005

(30) Foreign Application Priority Data
Dec. 22, 2001 (EP) ................................. 01310855

(51) Int. Cl.
*A01K 29/00* (2006.01)
*A01K 1/03* (2006.01)
*C12M 1/34* (2006.01)

(52) U.S. Cl. ................ 119/6.5; 119/420; 119/421; 435/287.1

(58) Field of Classification Search ................ 119/6.5, 119/400, 417–421, 712, 729, 416; 43/132.2; 436/66, 63; 435/4; 422/98
See application file for complete search history.

(56) References Cited
U.S. PATENT DOCUMENTS
2,093,784 A * 9/1937 Southwick ................. 119/6.5
(Continued)

FOREIGN PATENT DOCUMENTS
DE  195 36 389 A  4/1997
EP  0 439 001 A  7/1991

OTHER PUBLICATIONS

Voskamp, Karen E., et al.: "Electroantennogram responses of tsetse flies (*Glossina pallidipes*) to host odours in an open field and riverine woodland." Physiological Entomology, vol. 23, No. 2 Jun. 1998, pp. 176-183, XP002244509 ISSN: 0307-6962.

(Continued)

*Primary Examiner*—Teri Pham Luu
*Assistant Examiner*—Joshua Michener
(74) *Attorney, Agent, or Firm*—Morgan Lewis & Bockius LLP

(57) ABSTRACT

Apparatus for detecting a specific target odour comprises: a detector unit adapted to have removably associated therewith a holding unit for housing at least one insect in a predetermined position; means for exposing an insect in a holding unit associated with the detector unit to a sample of gas to be tested; and means for enabling monitoring of a response of the insect to the sample thereby to detect a response indicative of the target odour. In use of the apparatus, a holding unit housing at lest one insect that responds in a detectable manner to the target odour is associated with the detector unit. A sample of gas to be tested is supplied to the apparatus, for exposure to the insect or insects in the holding unit. The insect is monitored for a response indicative of the target odour, thus enabling determination as to whether or not the target odour is present in the sample. Because the holding unit is not part of the detector unit but is removably associated with therewith, the holding unit can be used to transport an insect or insects housed therein from a first, remote location, e.g. where insects are raised and conditioned, to a point of use at a second location where the detector unit is located. The detector unit may be a permanent or semi-permanent fixture at a point of use, or may be in the form of a portable unit. Also disclosed is a method of detecting a specific target odour.

12 Claims, 11 Drawing Sheets

U.S. PATENT DOCUMENTS

| | | | | |
|---|---|---|---|---|
| 3,367,308 | A | * | 2/1968 | Quattrone et al. .......... 119/420 |
| 3,874,335 | A | * | 4/1975 | Galasso ....................... 119/6.5 |
| 4,030,226 | A | * | 6/1977 | Shelton et al. ................. 43/55 |
| H145 | H | * | 10/1986 | James ....................... 600/529 |
| 5,031,573 | A | * | 7/1991 | De Marco et al. .......... 119/496 |
| 5,074,247 | A | * | 12/1991 | Gupta et al. ................. 119/6.5 |
| 5,297,502 | A | * | 3/1994 | Jaeger ....................... 119/420 |
| 6,651,587 | B1 | * | 11/2003 | DeFord et al. .............. 119/420 |
| 6,919,202 | B2 | * | 7/2005 | Lewis et al. ............. 435/287.1 |
| 7,036,454 | B2 | * | 5/2006 | Davis et al. ................. 119/6.5 |
| 2004/0118752 | A1 | * | 6/2004 | Simon et al. ............... 209/143 |

OTHER PUBLICATIONS

Sandoz, J.C., et al.: "Olfactory information transfer in the honeybee: compared efficiency of classical conditioning and early exposure" Animal Behavior, vol. 59, No. 5, 2000, pp. 1025-1034, XP002199430 Bailliere Tindall, London GB.

Pham-Delegue, M. H., et al.: "Behavioral Discrimination of Oilseed Rape Volatiles by the Honeybee *Apis mellifera* L" Chemical Senses, IRL Press, Oxford, GB vol. 18, No. 5, 1993, pp. 483-494, XP001064959.

* cited by examiner

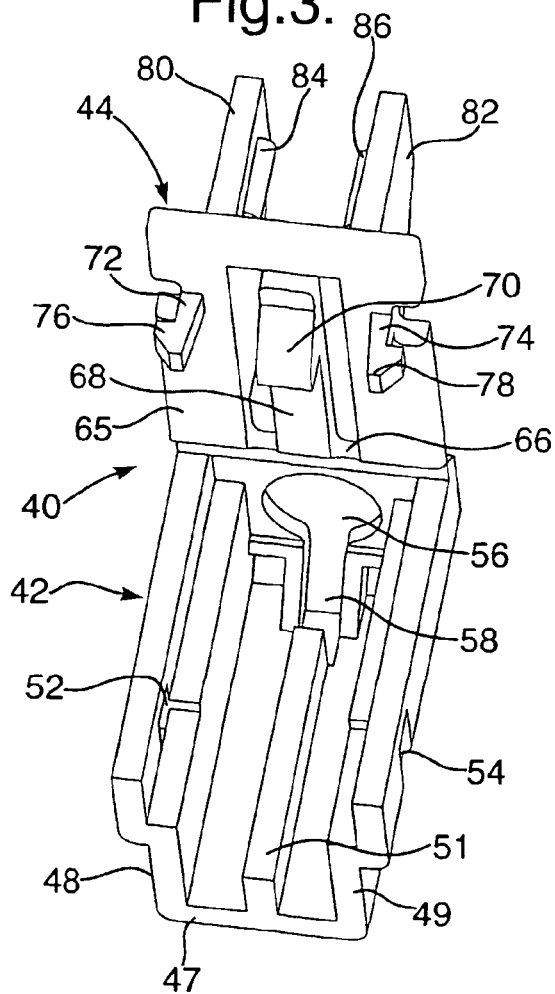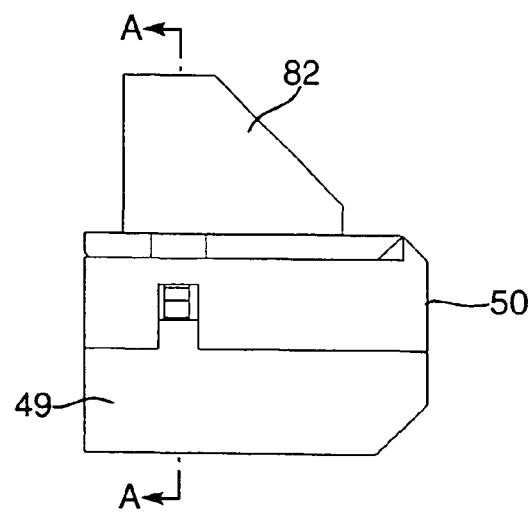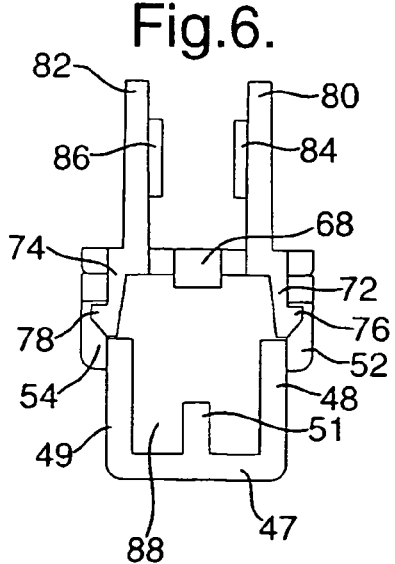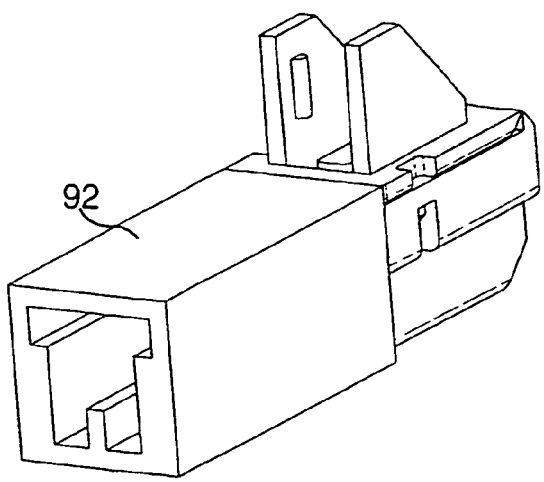

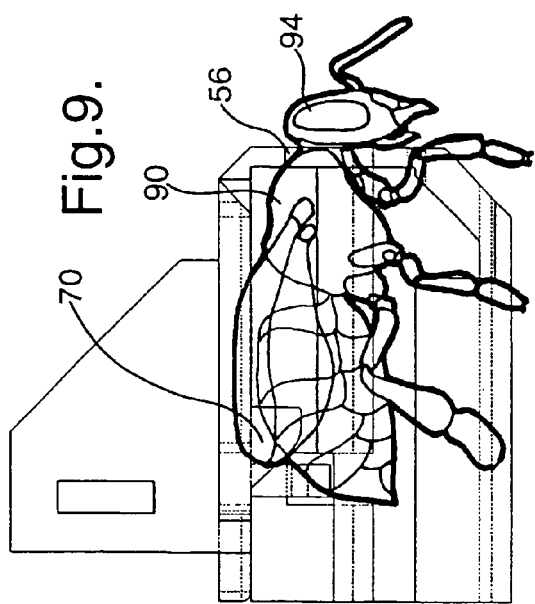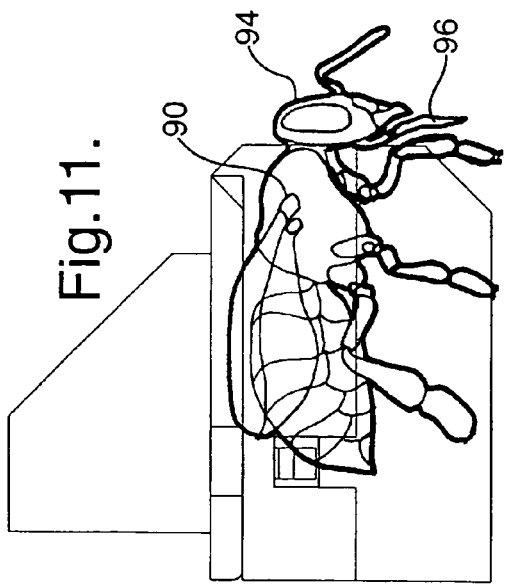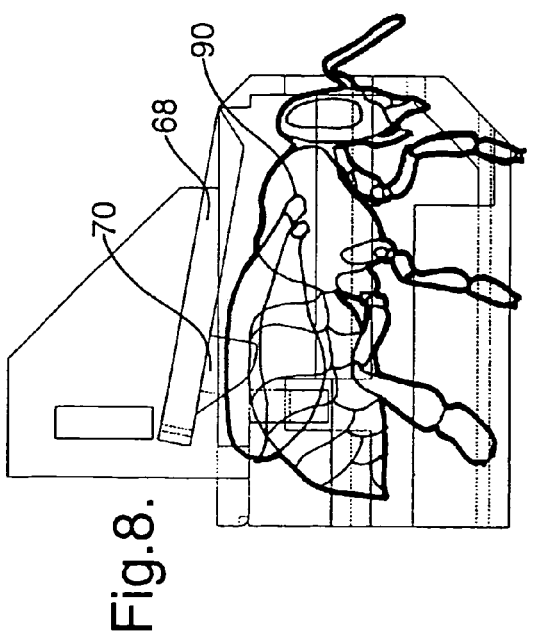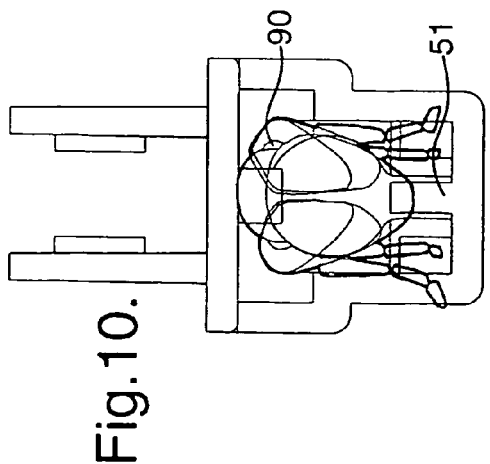

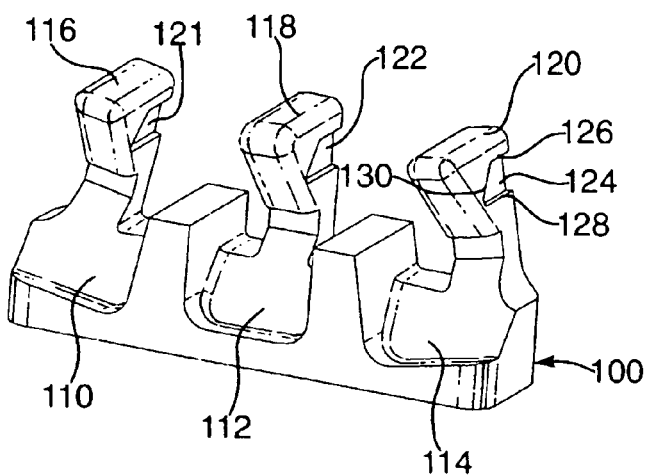
Fig.12.
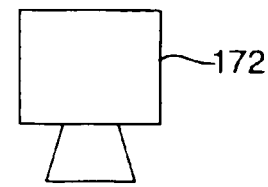
Fig.23
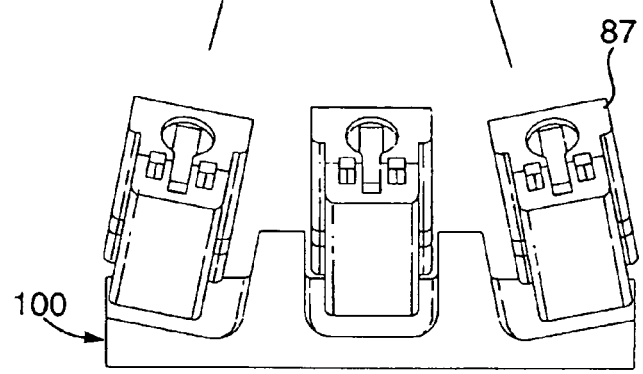
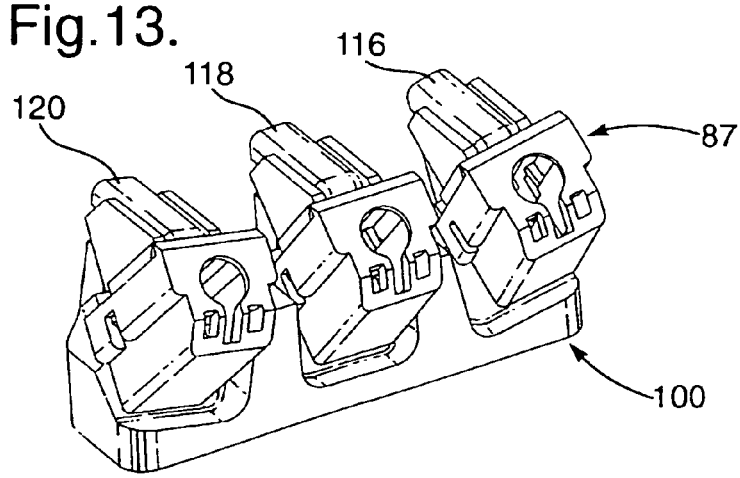
Fig.13.

DETECTION OF ODORS USING INSECTS

FIELD OF THE INVENTION

This invention relates to detection of odours and concerns apparatus and methods for detecting a specific target odour.

BACKGROUND OF THE INVENTION

It is known that animals such as dogs have good sensitivity to odours, with dogs being up to 200 times more sensitive to smell than humans. Such animals can be trained to respond in a particular detectable way to a specific odour. Trained sniffer dogs, for instance, are used to detect explosives, illegal drugs etc.

It is also known that insects can have much greater sensitivity to odours and can be more sensitive than the best physical techniques including gas chromatography, possibly being sensitive to odiferous materials present at very low levels down to $10^{-18}$ molar. Insects including bees, wasps, moths, aphids, etc can be trained or conditioned to respond with high accuracy and specificity to a specific odour in a detectable manner e.g. by measuring electrical signals in antennae (electroantennography) or observing physical movements such as proboscis extension. For instance, forager honey bees (species *Apis mellifera*) can be conditioned to a particular target odour, making a readily visible reflex proboscis extension response (see, e.g., Pham-Delegue M.-H., Bailez O., Blight M. M., Masson C., Picard-Nizou A. and Wadhams L. J. (1993) Behavioural discrimination of oilseed rape volatiles by the honeybee *Apix mellifera* L. *Chem.senses* 18: 483-494.).

Hitherto, insect responses of this sort have been generally only monitored in laboratories, e.g. for experimental purposes. Insects are not robust so practical difficulties arise over handling and transport of insects for use in other than laboratory conditions.

The present invention aims to facilitate wider use and exploitation of insect odour sensing abilities.

SUMMARY OF THE INVENTION

According to one aspect of the present invention there is provided apparatus for detecting a specific target odour, the apparatus comprising: a detector unit adapted to have removably associated therewith a holding unit for housing at least one insect (preferably two or more insects) in a predetermined position; means for exposing an insect in a holding unit associated with the detector unit to a sample of gas to be tested; and means for enabling monitoring of a response of the insect to the sample thereby to detect a response indicative of the target odour.

In use of the apparatus, a holding unit housing at least one insect (preferably two or more insects) that responds in detectable manner to the target odour is associated with the detector unit. A sample of gas to be tested is supplied to the apparatus, for exposure to the insect or insects in the holding unit. The insect is monitored for a response indicative of the target odour, thus enabling determination as to whether or not the target odour is present in the sample.

The insect used for detection of the odour is conveniently a bee, particularly a forager honey bee (species *Apis mellifera*). As noted above, bees can be conditioned, e.g. in known manner, to make a reflex proboscis extension response to a particular target odour. The proboscis extension response can be monitored, e.g. by known techniques such as Doppler radar, image analysis techniques etc. Bees have very good odour discrimination properties, for instance being able to distinguish between wrapped tobacco, wrapping material and unwrapped tobacco, enabling very precise odour detection. Bees are also sensitive to very low levels of odours, having substantially greater sensitivity than sniffer dogs, enabling reliable and precise detection of specific odours at very low levels. Other insects including wasps can also be similarly conditioned to respond to specific odours.

Certain insects may also have an innate reflex response to certain odours that can be exploited, without the need for insect conditioning.

While useful results may be obtained with a single insect in a holding unit, for reliability it is preferred to use two or more insects, typically 3 to 8, in a holding unit.

Because the holding unit is not part of the detector unit but is removably associated with therewith, the holding unit can be used to transport an insect or insects housed therein from a first location, e.g. where insects are raised and conditioned, to a point of use at a second location (possibly geographically distant from the first location) where the detector unit is located. The detector unit may be a permanent or semi-permanent fixture at a point of use, or may be in the form of a portable unit.

The holding unit is portable, that is, the unit is designed and adapted to be transported from one location to another (possibly geographically removed) location with insects housed therein. The holding unit is suitably robust to be able to be transported without damage being likely to occur to insects housed therein.

The present invention thus enables mass production, and possibly conditioning if required, of insects to be carried out at a first location, with insects being transported in a holding unit to an intended point of use at a second location in a way that has not hitherto been possible. In some cases it may be desired to condition the insects at the second location.

The invention also includes within its scope detecting apparatus as defined above in combination with an associated holding unit. The holding unit desirably has housed therein at least one insect (preferably two or more insects) in a predetermined position with respect to the holding unit and with respect to the detector unit.

In a further aspect the invention provides a holding unit for housing at least one insect (preferably two or more insects) in a predetermined position, the holding unit being adapted to be removably associated with a detector unit, for exposing an insect in the holding unit to a sample of gas to be tested and monitoring a response of the sample thereby to detect a response indicative of the target odour. The holding unit preferably has housed therein at least one insect (preferably two or more insects) that responds in detectable odour to a target odour.

The holding unit desirably includes or has associated therewith life support means for insect(s) located in the holding unit, typically including means for supplying nutrient such as sucrose solution for bees. In this way, insect(s) located in a holding unit can be sustained over an extended period of time, e.g. when in transit and in use, for instance up to about 7 days in the case of bees.

It is not essential for the holding unit to have means for supplying nutrient. For example, bees only need to be fed once every 24 hours, so they can survive in transit for up to 24 hours without food, provided environmental conditions, e.g. temperature, humidity etc are appropriate. Where the holding unit does not include means for supplying nutrient, the detector unit instead preferably includes or has associated therewith means for supplying nutrient. Environmental conditions, e.g. temperature, humidity etc within the detector unit should be appropriate for the insects.

The holding unit preferably comprises a support, carrier or housing and one or more removable insect holders, each for holding a respective insect of a particular type in a predetermined position. The holding unit typically includes a plurality, say 3 to 8, of similar insect holders, eg organised in a linear or (part) circular array on a support.

The detector unit is conveniently adapted to have a holding unit received therein in removable manner, e.g. by a holding unit being locatable in an appropriately configured aperture in the detector unit.

Desirably a plurality of similar holding units can be simultaneously associated with the detector unit, eg with the detector unit including a plurality of similar apertures as discussed above. The different holding units may each house one or more insects (preferably at least two insects) responsive to a different specific target odour, so that the detector unit and associated holding units can be used to detect a number of different target odours, possibly simultaneously in a single gas sample.

The means for exposing an insect in a holding unit in the detector unit to a sample of gas to be tested preferably comprises suitable ducting means, and desirably also includes means for creating a flow of gas past the insect, eg fan means or suction means.

The ducting means preferably terminates in one or more bell-ended tubes (one for each insect being tested), for supplying gas to the associated insect as a localised turbulent stream.

The sample of gas to be tested may be obtained from, e.g. the interior of a container lorry, freight container etc., e.g. using known techniques such as those currently used for obtaining samples for testing by sniffer dogs. The sample may be supplied directly to the detector unit for immediate testing, or stored in a container for later testing.

The means for monitoring a response of the insect to a sample conveniently comprises suitable image analysis equipment, for instance using a CCD camera. Because an insect is held in the holding unit in a predetermined position, the position of a particular part of the insect, eg the proboscis of a bee, is similarly predetermined, facilitating monitoring.

The exposing means and monitoring means conveniently form part of the detector unit.

The detector unit conveniently includes a source of light for illuminating insects therein, e.g. one or more arrays of LEDs. It is preferred to use red light for illuminating bees. A diffuser is conveniently provided between the light source and insects, for more even illumination. Surfaces of the detector unit behind and beside the holding unit and insets (in use) are desirably light coloured, e.g. white, to provide a contracting background against which the insects can be viewed by the monitoring means. e.g. CCD camera. The monitoring means is preferably vertically above the insects in the detector unit, in use.

Suitable display means and/or recording means are desirably associated with the monitoring means, for displaying and/or recording the results of monitoring.

The holding unit is conveniently reusable. In this case, after use in a particular detector unit, a holding unit and the insect or insects located thereon may be returned to the first location or a similar location. The used insects may either be retired or released or reconditioned for further use. This is to be contrasted with prior art practices in which insects are generally treated as disposable, being discarded after a single use often in poor or dead condition The returned holding unit can be reused by having further insects housed therein, for supply to the same detector unit or a similar detector unit.

In a further aspect the invention provides a system for detecting one or more specific target odours, the system comprising: a plurality of detector units, each unit being adapted to have removably associated therewith a holding unit for housing at least one insect (preferably two or more insects) in a predetermined position, and each detector unit including or having associated therewith means for exposing an insect in an associated holding unit to a sample of gas to be tested and means for enabling monitoring of a response of the insect to the sample thereby to detect a response indicative of the target odour; and a plurality of holding units, wherein the holding units and detector units are interchangeable, with any holding unit being usable with any detector unit. Typically the holding units are similar or identical.

Insects can thus be supplied in the holding units to any detector unit in the system from one or more first locations for raising, and possibly also conditioning, the insects. Similarly, after use the holding units can be returned to the first location or locations for recycling and reuse, for possible re-supply to any detector unit in the system.

The invention also provides a method of detecting a specific target odour, the method comprising associating with a detector unit a holding unit housing at least one insect (preferably two or more insects) in a predetermined position, the insect responding in a detectable manner to the target odour; exposing the insect to a sample of gas to be tested; and monitoring a response of the insect to the sample thereby to detect a response indicative of the target odour.

The invention finds potential application in a wide range of fields, including detecting concealed goods such as tobacco, illegal drugs etc for customs purposes, explosives for security purposes, medical diagnostics, food quality and safety, forensics etc.

In a further aspect the invention provides a method of detecting a specific target odour, the method comprising: at a first location housing at least one insect (preferably two or more insects) in a predetermined position in a holding unit; transporting the holding unit and insect or insects housed therein to a second location where a detector unit is located; associating the holding unit with the detector unit at the second location, the insect in the detector unit responding in a detectable manner to the target odour; exposing the insect or insects to a sample of gas to be tested; and monitoring a response of the insect or insects to the sample, thereby to detect a response indicative of the target odour.

The first location is typically a central location where insects are raised, and possibly also conditioned to respond to a particular target odour. The second location is a geographically separate point of use, and may be in fixed location such as a customs and excise checkpoint at an airport or seaport, a factory etc, where a detector unit may be permanently or semi-permanently located, or a movable location where a portable detector unit is located.

The insects may alternatively or additionally be conditioned if required at the second location.

Conditions within the holding unit and detector unit should be such as to sustain the insect or insects over an extended period of time, when in transit and in use, for instance up to about 7 days in the case of bees.

After use at the second location, for several days in the case of bees, the holding unit is removed or dissociated from the detector unit and returned, preferably still housing the insect or insects, to the first location or a similar location for insect handling. There the insects may be retired, released or possibly reconditioned for further use. The holding unit can be similarly reused by having further insects housed therein for supply to a detector unit.

The invention will be further described, by way of illustration, with reference to the accompanying drawings, in which:

FIG. 3 is a view from the rear and above of the bee holder moulding shown in FIGS. 1 and 2;

FIG. 5 is a view from the right side of the bee holder shown in FIG. 4;

FIG. 6 is a sectional view along line A-A in FIG. 5;

FIG. 7 is a view from the rear and right side of the bee holder shown in FIGS. 4 to 6 with an attached loading tunnel;

FIG. 8 is a schematic longitudinal sectional view illustrating a bee entering the bee holder shown in FIGS. 4 to 7;

FIG. 9 is a view similar to FIG. 8 showing a bee fully located in the bee holder;

FIG. 10 is a front view illustrating a bee holder in the shown in FIGS. 4 to 9;

FIG. 11 is a side view of a bee in the bee holder of FIGS. 4 to 10, with the proboscis of the bee extended;

FIG. 12 shows a support seen from the front and one side (the left side) for holding 3 bee holders as shown in FIGS. 4 to 11 to form a holding unit;

FIG. 13 shows a holding unit comprising the support of FIG. 12, seen from the front and the other side, holding 3 bee holders;

FIG. 23 is a schematic end view of the holding unit of FIG. 13 in the detector unit of FIGS. 14 to 21;

DETAILED DESCRIPTION OF THE DRAWINGS

Figure 1:
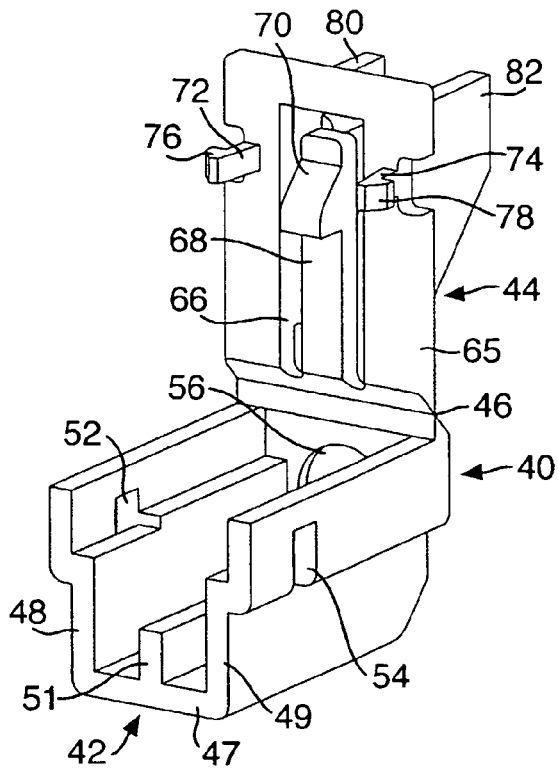
FIG. 1 is a view from the rear and one side (the right side) of a moulding for a bee holder for use with embodiments of the invention.
Figure 2:
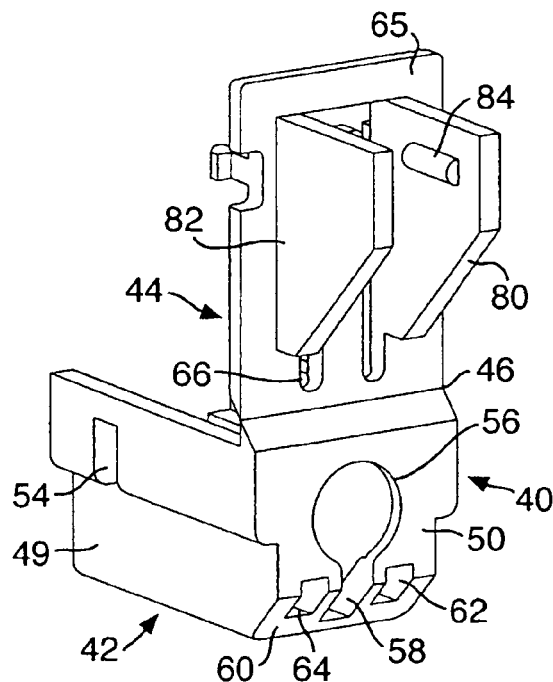
FIG. 2 is a view from the front and right side of the bee holder moulding shown in FIG. 1.
Figure 4:
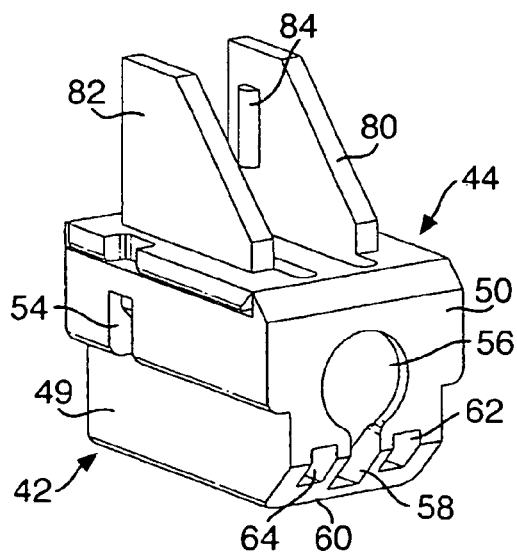
FIG. 4 is a view from the front and right side of a bee holder formed from the moulding shown in FIGS. 1 to 3.

FIGS. 1 to 11 illustrate an embodiment of bee holder made from a one piece polypropylene moulding 40, as shown in FIGS. 1 to 3, manufactured using an open and shut injection moulding tool. The moulding comprises a lower channel portion 42 and an upper lid portion 44 connected by a thin web 46 (shown schematically in the drawings) that constitutes an integral hinge.

The lower channel portion 42 includes a bottom wall 47, side walls 48 and 49 and a front wall 50. The rear of the lower channel portion is open. A longitudinal rib 51 extends upwardly from the bottom wall 47. The side walls 48 and 49 are each of stepped configuration and include a respective opening 52, 54 for closure purposes, to be discussed below. The front wall has a circular opening 56 therein, with a central slit 58 extending downwardly therefrom and terminating in a lower inclined portion 60 of the front wall. A respective rectangular opening, 62, 64 is provided in the front wall, on each side of the slit 58.

The upper lid portion 44 includes a generally planar cover member 65, with a central opening 66 in which is located a tongue 68 having a barb 70 adjacent the free end thereof for trapping and retaining a bee in the holder, as will be discussed below, thus constituting retaining means. A pair of arms 72, 74 extend perpendicularly from the underside of the lid portion 44, each terminating in a respective outwardly directed flange portion 76, 78 for engaging in the openings 52, 54 for closure purposes. A pair of generally triangular fins or mounting clips 80, 82 extend perpendicularly from the upper side of the lid portion 44, with a respective location rib 84, 86 on the adjacent inner faces of the clips.

A bee holder 87 is produced from the moulding 40 by pivoting the portions 42 and 44 towards each other, around hinge 46, so that the lid portion 44 overlays the channel portion 42 as shown in FIGS. 4 to 11. FIGS. 8 to 11 include a schematic representation of a bee in the holder. The arms 72, 74 are sufficiently resiliently deformable to enable the flange portions 76, 78 to move within the lower channel portion yet engage in the openings 52, 54, thus locking the lid portion 44 into position on the lower channel portion with a snap fit (FIG. 6). The resulting bee holder is of generally box-like form, having an overall length of 14 mm, an overall height of 9 mm (excluding the upstanding mounting clips), a maximum width of 9 mm, with a narrower lower portion 7 mm wide. The holder defines a generally box-like chamber 88, having a width in the lower portion of 5 mm. The clearance between the top of the rib 51 and the underside of the cover member 65 (and tongue 68) is 5 mm, with the spacing between the top of the rib 51 and the barb 70 being 3.5 mm. The rib 51 is 1.8 mm wide. The open rear of the lower channel portion constitutes an inlet to the chamber, and the circular opening 56 (which has a diameter of 4 mm) in the front wall constitutes a head opening for a bee located in the chamber.

In use, a forager honey bee 90 is inserted into the chamber 88 through the inlet constituted by the open rear of the lower channel portion, head first. The bee may be inserted manually by a skilled handler. Alternatively, the bee may be lured to enter the chamber by use of one or more attractants suitably positioned downstream of the chamber. The bee may enter the chamber via a loading tunnel 92, of similar internal cross-sectional form to the chamber, as shown in FIG. 7. As the bee enters the chamber, the tongue 68 is moved upwardly, as shown in FIG. 8, on engagement of barb 70 with the back of the abdomen of the bee. When the bee has fully entered the chamber, with the head 94 of the bee protruding through the opening 56, as shown in FIG. 9, the tongue resumes its original position due to the resilient nature of the material, with the barb 70 located behind the rear of the abdomen of the bee thus preventing the bee from leaving the chamber via the inlet. The tongue and barb thus function as a one-way valve, permitting entry of a bee to the chamber but preventing exit. Opening 56 is appropriately dimensioned to permit the head but not the body of the bee to pass therethrough, so the body of the bee is retained in the chamber. The barb 70 thus functions as retaining means. The chamber 88 is dimensioned to provide sufficient space for the bee to be accommodated therein, while preventing the bee from turning around or withdrawing its head into the chamber. The rib 51 assists in orienting the bee in the chamber, with the underside of the body of the bee being able to rest on the rib and the two rear pairs of legs of the bee possibly gripping the sides of the rib. The front pair of legs of the bee can pass through the openings 62, 64, further assisting in orienting the bee in the chamber. The wings of the bee are comfortably accommodated in the slightly wider upper region of the chamber 88.

With the bee restrained in the holder, observations of the head can be made, particularly of extension of the proboscis 96, as illustrated in FIG. 11, with the slit 58 being positioned to facilitate proboscis extension outside the chamber and so facilitate monitoring thereof.

When observations have finished, the lid portion 44 may be pivoted away from the lower channel portion 42 around hinge 46, thus opening the chamber and permitting the bee to leave the chamber in undamaged and unharmed condition.

FIG. 12 illustrates a support or carrier 100 adapted to have removably secured thereto 3 bee holders 87 as described above with reference to FIGS. 4 to 11, to form a holding unit. The support 100 comprises a one piece polypropylene moulding having 3 recesses 110, 112 and 114 each with an associated upstanding lug 116, 118 and 120, respectively. Each lug includes a pair of similar recesses on opposed sides thereof, only one recess 121, 122 and 124 being visible in FIG. 12. Each recess is open at one end (at the rear of the holding unit 100), has parallel upper and lower side walls (e.g. 126 and 128) and terminates in an inclined inner end wall (e.g. 130) at an angle of about 45° to the associated lower side wall 128.

A bee holder 87 as described above is secured to a lug of the support 100 by means of the mounting clips 80, 82 and location ribs 84, 86. A holder is tilted through an angle of about 45°, with the front wall 50 above the open rear of the holder. The spacing between the clips 80, 82 is slightly larger than the width of a lug so that the clips can be secured on a lug as a push fit from the front, with the clips deforming resiliently to a sufficient degree to permit the ribs 84, 86 to pass over the lug and fit into the recesses as a snap fit, with the ribs engaging the inclined inner end walls of the recesses. In this way a bee holder can be firmly yet removably secured to the support, as shown in FIG. 13, forming a holding unit. In practice, a bee would first be located in a holder and the holder with bee secured to the support, with the bees thus in a predetermined position, but for clarity and simplicity bees are not shown in FIG. 13.

Figure 14:
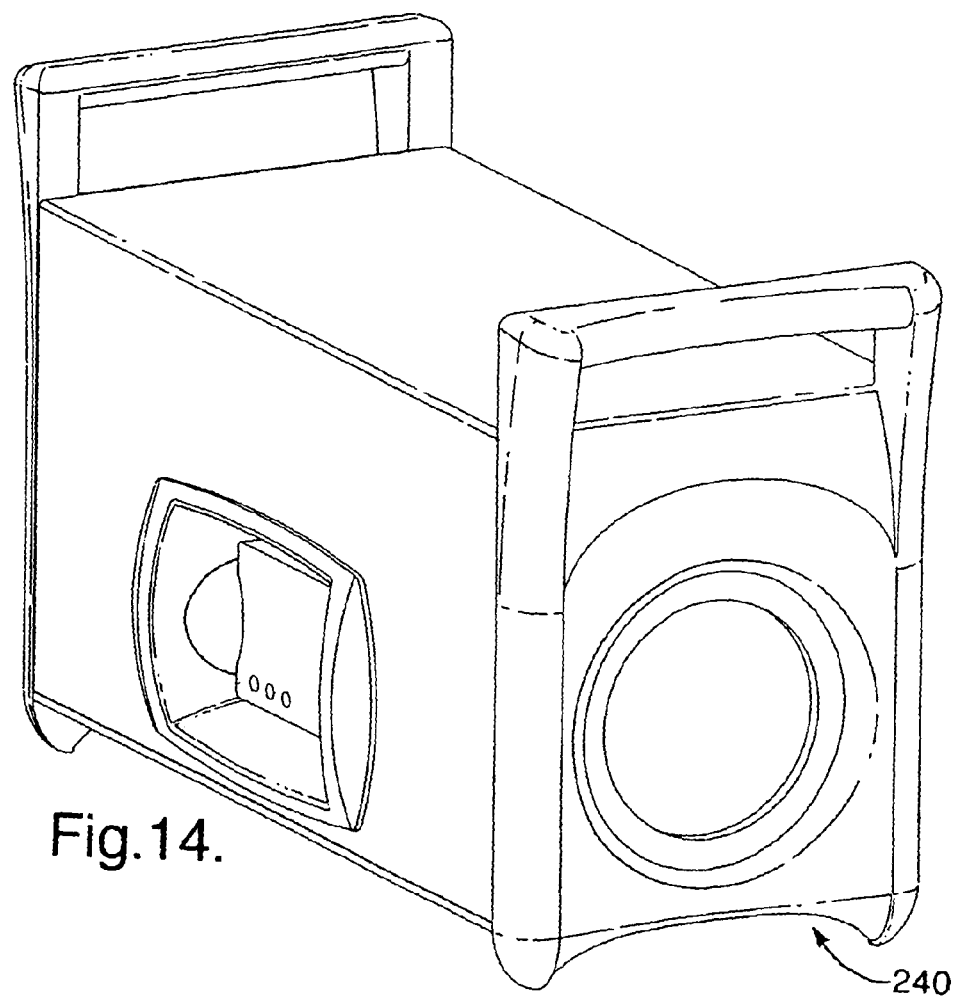
FIG. 14 is a view from the front and one end of a detector unit.
Figure 15:
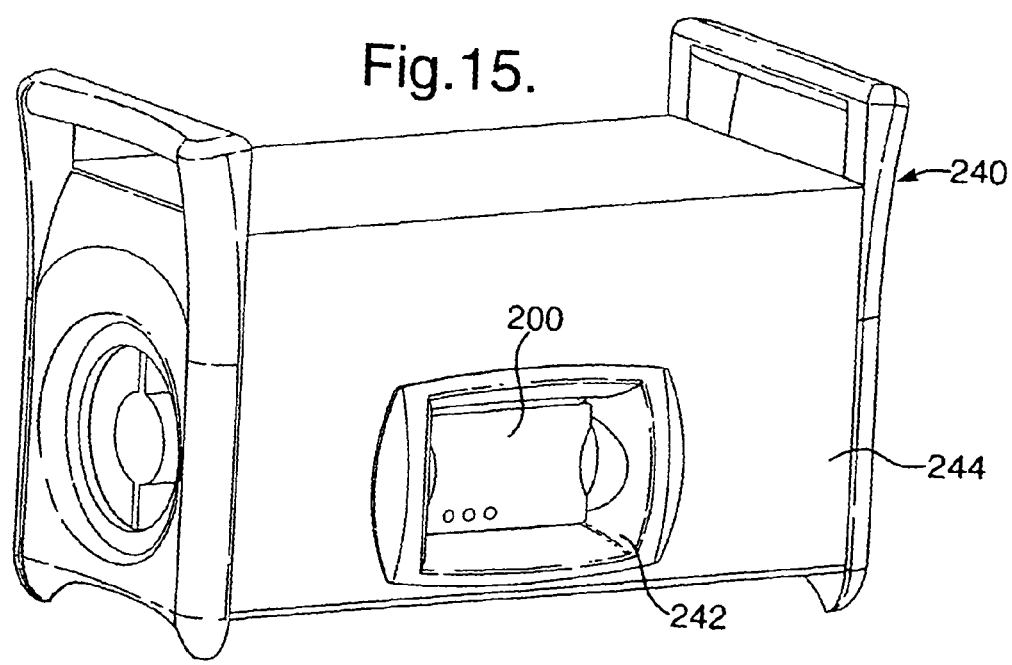
FIG. 15 is a view from the front and other end of the detector unit of FIG. 14.
Figure 16:
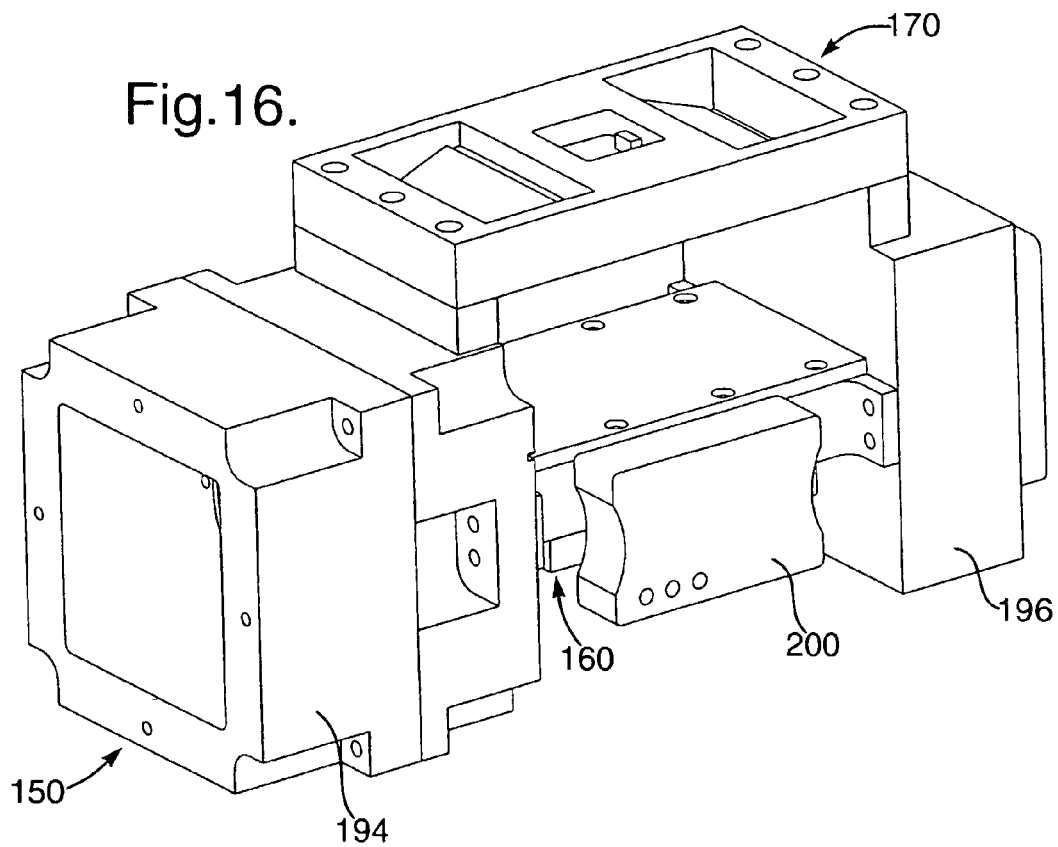
FIG. 16 is a view from the rear and the one end of the internal components of the detector unit of FIGS. 14 and 15.
Figure 17:
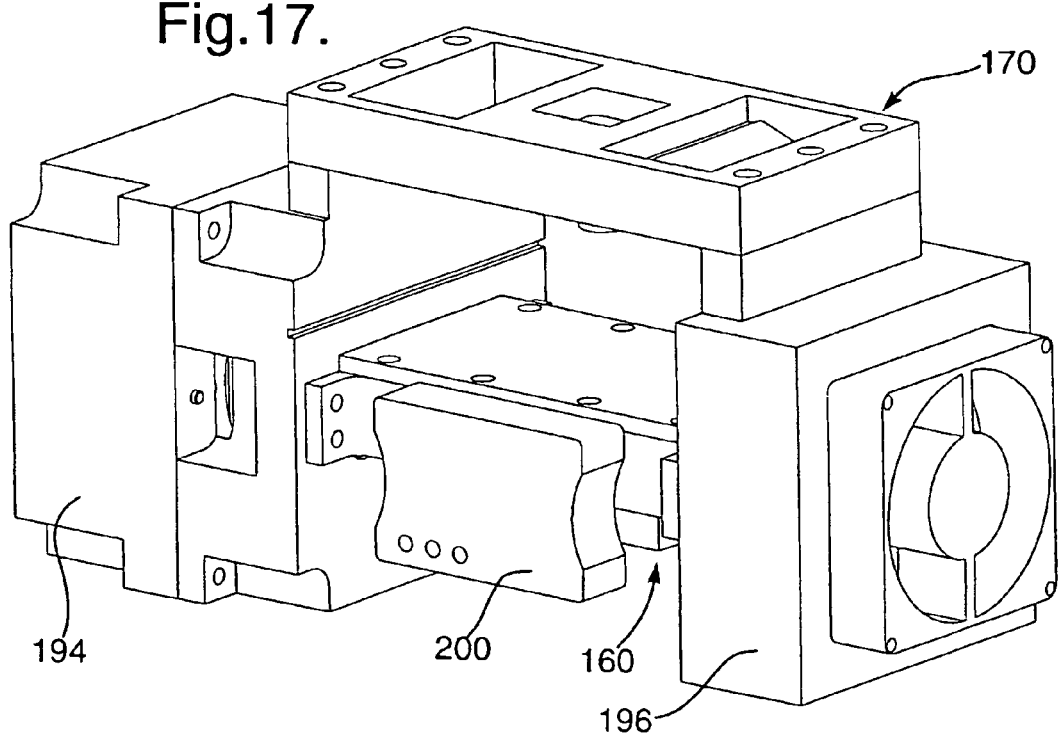
FIG. 17 is a view from the rear and the other end of the internal components of the detector unit of FIGS. 14 and 15.
Figure 19:
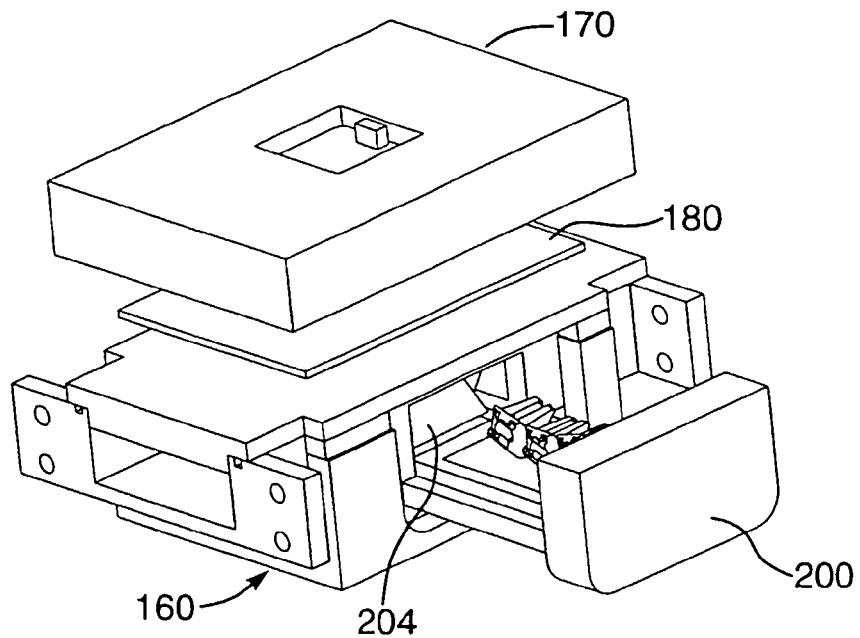
FIG. 19 is a schematic illustration of some of the internal components of the detector unit of FIGS. 14 to 18.
Figure 18:
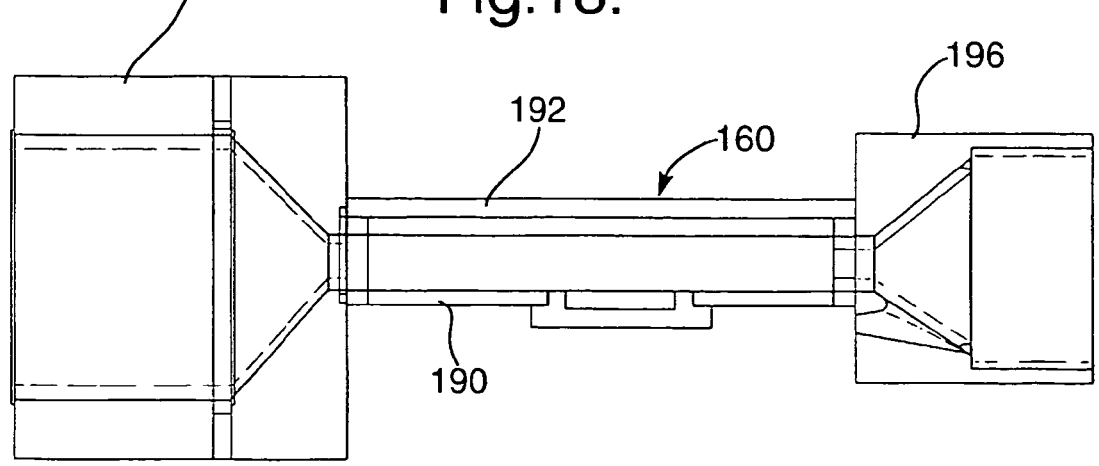
FIG. 18 is a schematic illustration of the air flow system of the detector unit of FIGS. 14 to 17.
Figure 20:
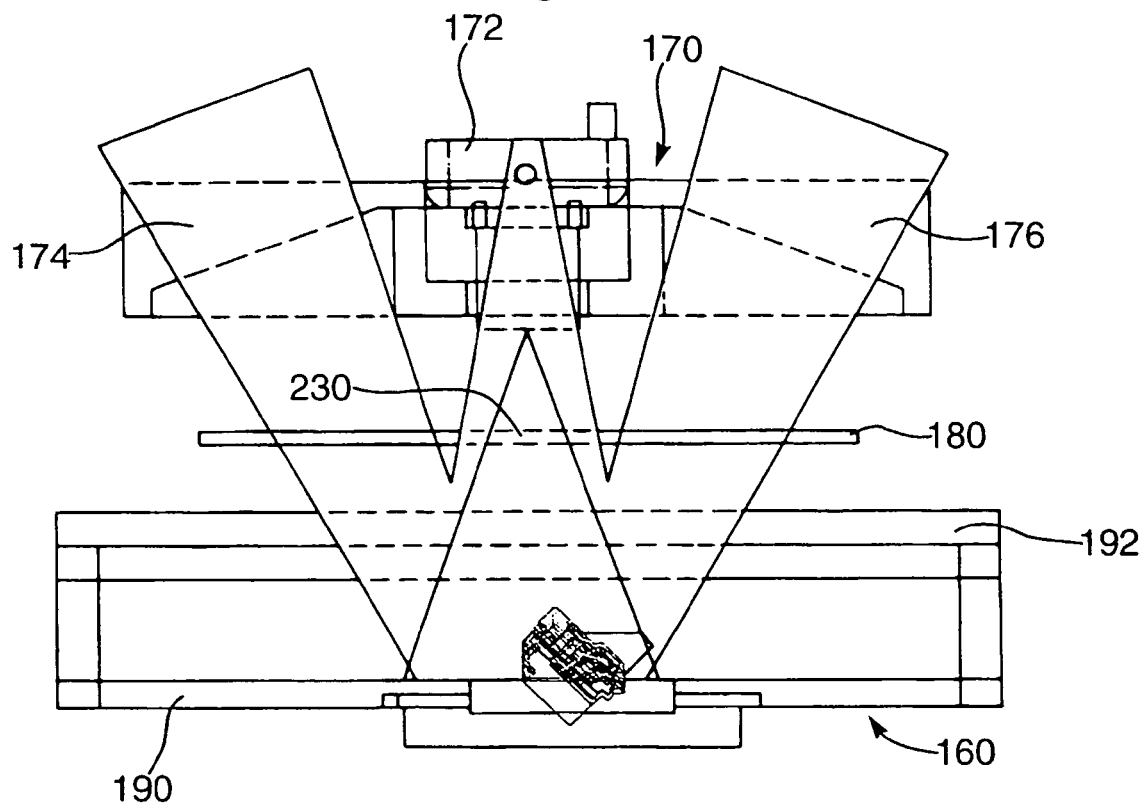
FIG. 20 is a schematic side view of the components shown in FIG. 19.

The holding unit including support 100 is designed for use with a detector unit 150 as illustrated in FIGS. 14 to 23. The main internal components of the detector unit 150 are shown in FIGS. 16 and 17, with FIGS. 18 to 23 showing various components and details, and FIGS. 14 and 15 showing the overall external appearance.

The detector unit 150 comprises a lower chamber assembly 160 for receiving a holding unit including support 100 with bees and having an associated air flow system and gas sample supply system; an upper assembly 170 including a CCD camera 172 and light emitting diode (LED) light sources 174 and 176; and a diffusing plate 180 between the upper and lower assemblies.

The lower chamber assembly 160 comprises an elongate, open-ended channel 190 having bottom and side walls of polytetrafluoroethylene (PTFE) and a top wall 192 of optical quality polycarbonate sheet. One end of the channel 190 is secured to a housing 194 including an activated carbon filter, and constituting an air inlet to the channel. The other end of the channel is secured to a housing 196 including a fan with rubber vibration isolation mounting for drawing filtered air through the channel. A loading tray 200 including a recess 202 adapted to receive a holding unit including support 100 (FIG. 22) is slidably receivable in an opening 204 in one of the side walls of the channel 190 (FIG. 19) to locate bees carried by the holding unit within the channel. The tray 200 is provided with suitable 'O' ring seals that interface with appropriate surfaces on the channel to provide an air tight seal.

Figure 21:
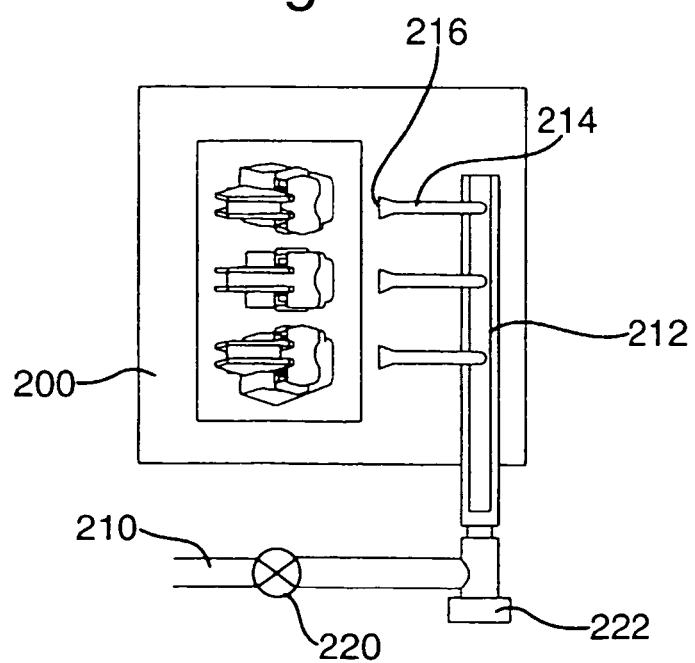
FIG. 21 is a schematic plan view of a detail of the internal components of the detector unit of FIGS. 14 to 20.
Figure 22:
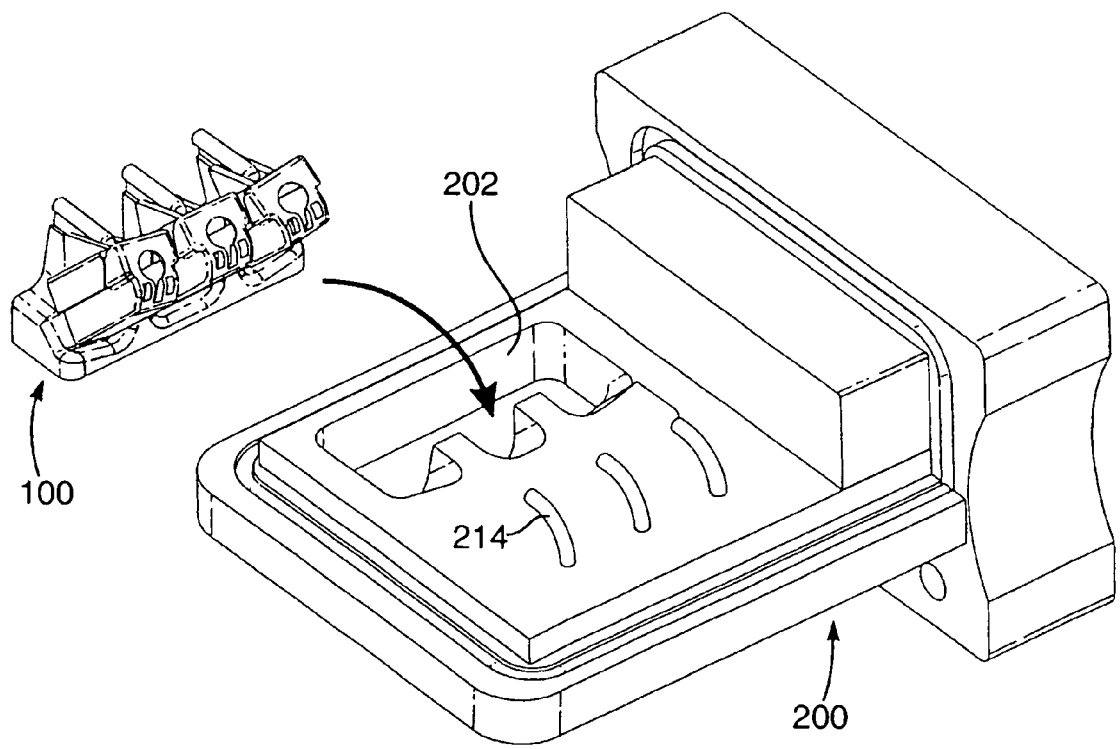
FIG. 22 shows part of the detector unit of FIGS. 14 to 21 together with the holding unit of FIG. 13.

As shown in FIGS. 21 and 22, the tray 200 includes a gas sample supply arrangement, including an air supply tube 210 leading from similar the main supply of filtered air through the channel 190, passing to glass tubing 212 with 3 similar side branches 214 each terminating in a 'bell end' 216 (not shown in FIG. 22) for supplying gas as a turbulent stream to hit the antennae of a respective bee held in holding unit including support 100 in the loading tray 200. The branches 214 supply sample gas to the bees, just in front of and upstream of the bee heads, in line with the main air flow through the chamber. Tube 210 includes an on/off valve 220 for controlling flow of air, and a septum valve 222 for injecting a gas sample to be tested into the system.

The upper assembly 170 includes CCD camera 172. The camera is mounted to be aligned with the heads of bees held in a holding unit 100 in the channel 190. As illustrated in FIG. 23, bee holders 87 secured to the support 100 are slightly inclined with respect to each other, with the degree of inclination being such that the heads of bees in the holders are oriented towards the centre of the camera lens so that proboscis extension movement viewed from above by the camera is seen normal to the field of view for all 3 bees. The camera 172 is linked to a personal computer (PC) (not shown) suitably programmed to rain an image analysis program to measure the extension, if any, of the proboscis of bees in the chamber, and to store and/or display the results.

The LED light sources 174 and 176 each comprises an array of 20 red LEDs oriented at an angle so that the emitted light is reflected off the bee holding unit including support 100, the upper surface of the loading tray 200, and the base of channel 190 (these components being white to provide a contrasting surface against which to view the dark matt bee head and proboscis) into the camera lens. The light is diffused as it passes through the diffusing plate 180, providing a more even illumination. A rectangular hole 230 is provided in the centre of the diffusing plate to enable light to pass to the camera.

The detector unit components are housed in a fox-like outer enclosing 240 (shown in mirror image in FIGS. 14 and 15), including an opening 242 in a side wall 244 to permit opening and closing of loading tray 200 to permit loading and unloading of bees. The detector unit includes environmental control means (not shown), including a Thermistor-controlled element in the airstream for regulating temperature and means for regulating the humidity of air being supplied to bees therein. The detector unit can be powered externally from a main electricity supply, and/or can include a battery power supply (not shown) to provide a portable unit suitable for use in the field.

In use of the apparatus, a holding unit including support 100 housing 3 bees (in respective holders 87) conditioned to respond to a particular target odour by making a reflex proboscis extension response is located in the loading tray 200 (FIG. 22—bees omitted for clarity) and the loading tray 200 located in the lower chamber assembly in sealing manner.

Filtered air at a temperature between 22 and 28° C. and at suitable humidity is drawn through the channel 190, over the bees by the fan to pass in a laminar flow at a velocity across the bees of about 0.4 m/s.

A gas sample to be tested is obtained e.g. from a vehicle body either by direct air sampling or concentrated sampling. The gas to be tested is supplied to the bees via the sample injection system. Normally, valve 220 is open and filtered air tapped from the main air supply to the channel 190 is fed in by means of a secondary fan (not shown) through tubing 210, 212 and 214 at a velocity of about 0.4 m/s to flush the tubing continuously and prevent any contaminant build-up. The septum valve 222 is used to inject into the system a gas sample for testing. The valve 220 is closed when this occurs, so the sample gas replaces the usual flow of filtered air. The gas sample passes through tubing 212 and branches 214, exiting via nozzle ends 216, producing a turbulent stream of air to hit the antennae of the bees in the unit. The gas sample is provided by placing a concentrated sample of the test gas sample into a glass tube with a needle like end, and an open end. The open end is connected to a fluid line, which is connected to a pump, via a switch operated valve, which produces a build up of pressure. The needle like end is inserted through the septum valve, and the volatiles from the concentrated air samples are allowed to build up sufficiently before the switch operated valve is released, allowing the volatile sample to be presented to the bees at a velocity of 0.4 m/s.

The bell ends 216 to the tubing branches 214 produce a localised turbulent flow, which spreads the sample over a greater area and ensures the flow passes over the bee antennae. Without this feature the sample would be supplied in a laminar flow such that the sample stream would be likely to miss the bees due to aerodynamic effects.

The camera 172 monitors the heads of the bees and detects any proboscis extension movement in response to the sample. The results are displayed and/or recorded on the associated PC.

Figure 24:
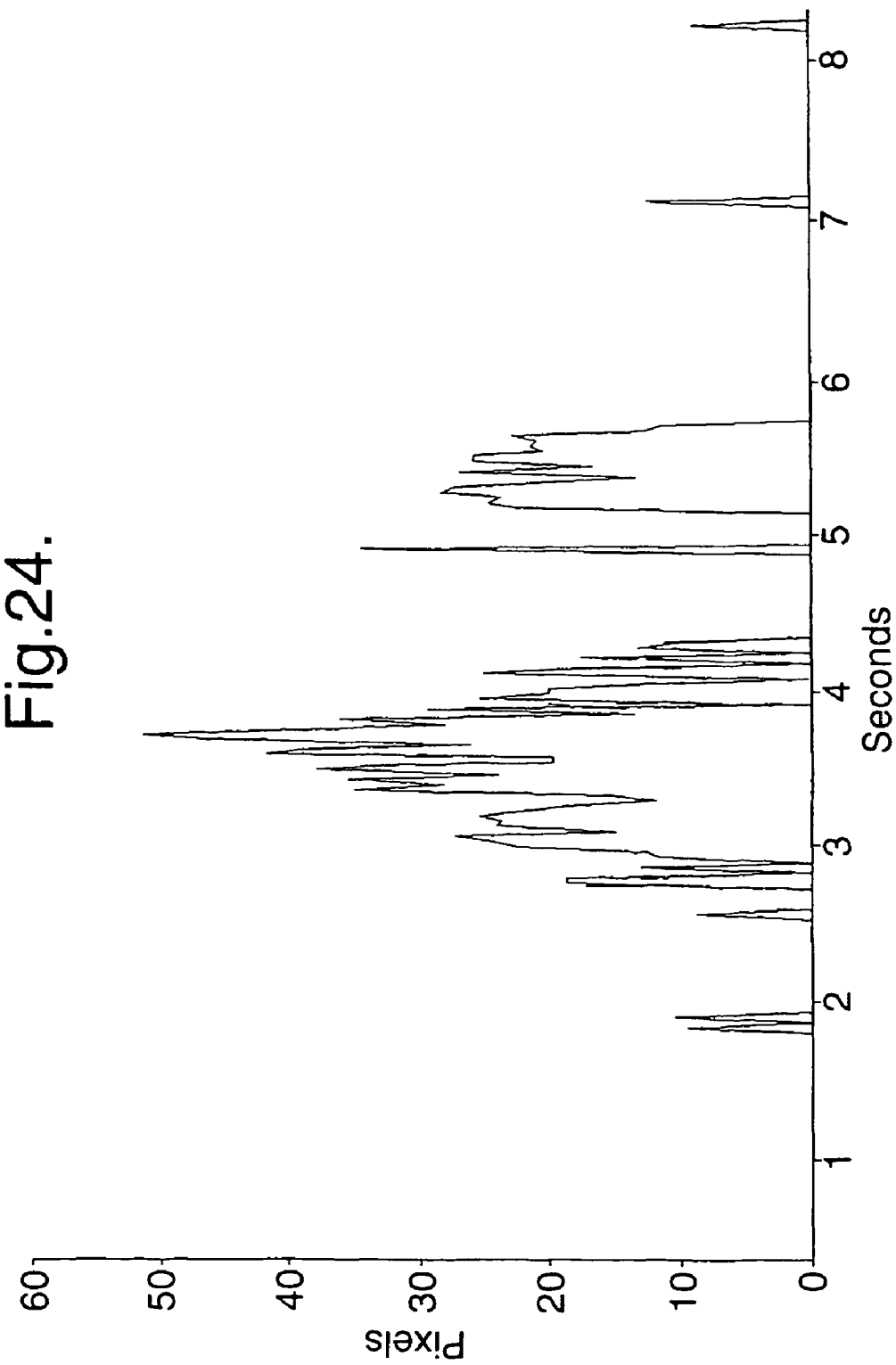
FIG. 24 is a graph of number of pixels versus time (seconds) representing proboscis extension versus time obtained using apparatus of the invention.

Typical results are shown in FIG. 24, which shows proboscis extension (measured in pixels) versus time in response to exposure to sample gas containing volatile materials produced from wrapped tobacco, introduced at time 0.

In a modification of the above described detector unit, the lower chamber portion is designed to receive 2 or more similar holding units, e.g. in side by side relationship by having 2 similar loading units. Each holding unit in the detector unit has appropriate gas sample supply means associated therewith. A single camera may be able to monitor all bee responses, but it may alternatively be necessary to provide one or more additional cameras. Such an embodiment may be used, for example, to detect two different target odours in a single sample, e.g. wrapped tobacco and unwrapped tobacco.

Figure 25:
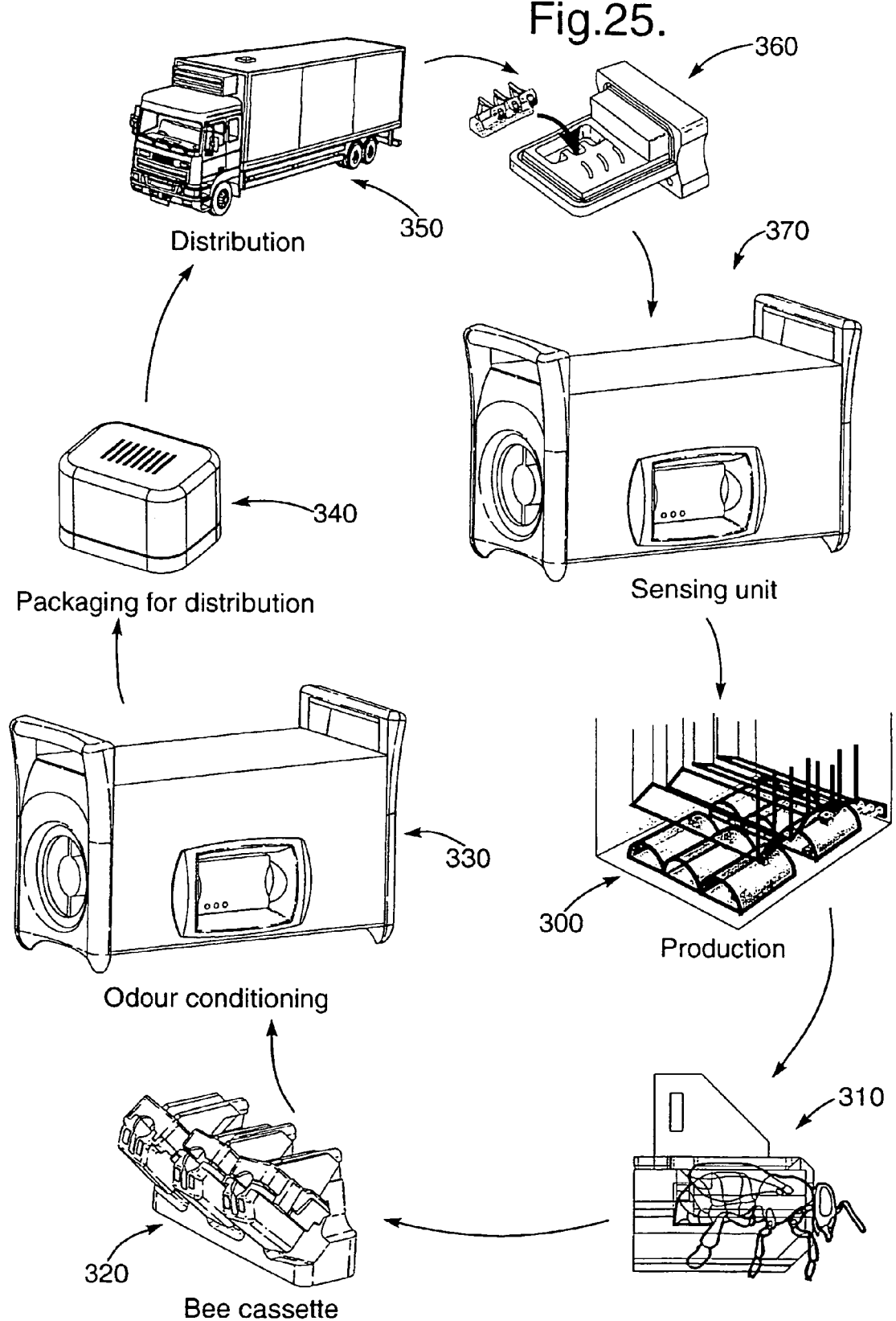
FIG. 25 illustrates schematically one aspect of the method of the invention.

The apparatus finds use in an overall arrangement as illustrated in FIG. 25. Bees are produced as represented at 300 at a first location. Bees of a suitable stage of development are loaded into bee holders 87, as represented at 310, and secured to a support 100 to form a holding unit, as represented at 320. The holding unit is placed in a detector unit 150 and the bees conditioned, e.g. in known manner, to respond to a particular target odour by making a reflex proboscis extension response, as represented at 330. The holding unit is then removed from the detector unit and packaged for distribution as represented at 340, being maintained under suitable conditions of temperature and humidity. All of the above steps take place at the first location.

The bees are then distributed by a lorry, as represented at 350, to a point of use at a second location. The bees only need to be fed once a day, and so can survive up to 24 hours in transit. At the second location, the holding unit is loaded into the drawer of a further, similar detector unit 150, as represented at 360 and 370. Gas samples to be tested for the particular odour to which the bees are conditioned to respond are supplied to the detector unit, and proboscis extension measurements made as described above.

The bees are fed with sucrose solution as required at the first and second locations, with the bees being maintained at all times in suitable environmental conditions to keep the bees alive and in good condition. Bees can be maintained in this way for up to 7 days.

When use at the second location is finished, the holding unit with the bees is returned to the first location by lorry. The bees are released from the holders, to be released retired or reconditioned for further use, as required.

Uses of the bees include detecting concealed goods such as tobacco, illegal drugs etc for customs purposes, explosives for security purposes, medical diagnostics, food quality and safety, forensics etc.

The invention claimed is:

1. Apparatus for detecting a specific target odour, the apparatus comprising: a detector unit and means for receiving a removable holding unit, wherein the removable holding unit has means for housing at least one insect in a restrained predetermined position such that the insect is prevented from turning around the detector unit comprising the removable holding unit received therein; means for exposing an insect when restrained in the removable holding unit to a sample of gas to be tested; and means for enabling monitoring of a response of the insect to the sample thereby to detect a response indicative of the target odour.

2. Apparatus according to claim 1, wherein the removable holding unit has housed therein at least one insect in a restrained predetermined position.

3. Apparatus according to claim 2, wherein at least one of the detector unit and the removable holding unit includes or has associated therewith means for supplying nutrient to insect(s) housed in the holding unit.

4. Apparatus according to claim 2, wherein the removable holding unit comprises a support, carrier or housing and one or more removable insect holders, each for holding a respective insect of a particular type in a restrained predetermined position.

5. Apparatus according to claim 4, wherein the removable holding unit includes a plurality of similar insect holders.

6. Apparatus according to claim 1, wherein a plurality of removable holding units can be simultaneously associated with the detector unit.

7. Apparatus according to claim 1, wherein the means for exposing an insect in a holding unit in the detector unit to a sample of gas to be tested comprises suitable ducting means, and desirably also includes means for creating a flow of gas past the insect.

8. Apparatus according to claim 7, wherein the ducting means terminates in one or more bell-ended tubes, for supplying gas as a localized turbulent stream.

9. Apparatus according to claim 1, wherein the means for monitoring a response of the insect to a sample is comprised of image analysis equipment.

10. A system for detecting one or more specific target odours, the system comprising: a plurality of detector units and removable holding units, each detector unit comprising means for receiving one of the removable holding units, wherein the removable holding units have means for housing at least one insect in a restrained predetermined position such that the insect is prevented from turning around, each detector unit comprising one of the removable holding units received therein, and each detector unit includes means for exposing an insect in the removable holding unit to a sample of gas to be tested and means for enabling monitoring of a response of the insect to the sample thereby to detect a response indicative of the target odour; and the removable holding units and detector units are interchangeable such that any holding unit is usable with any detector unit.

11. A method of detecting a specific target odour, the method comprising receiving a holding unit in a detector unit a detector unit the holding unit housing at least one insect in a restrained predetermined position such that the insect is prevented from turning around, the insect responding in a detectable manner to the target odour; exposing the insect to a sample of gas to be tested when thus restrained in the holding unit; and monitoring a response of the insect to the sample thereby to detect a response indicative of the target odour.

12. A method of detecting a specific target odour, the method comprising: at a first location housing at least one insect in a restrained predetermined position in a holding unit such that the insect is prevented from turning around; transporting the holding unit and insect or insects housed therein to a second location where a detector unit is located; receiving the holding unit in the detector unit at the second location, the insect in the detector unit responding in a detectable manner to the target odour; exposing the insect or insects to a sample of gas to be tested when thus restrained in the holding unit; and monitoring a response of the insect or insects to the sample, thereby to detect a response indicative of the target odour.

* * * * *